United States Patent [19]
Poziomek et al.

[11] Patent Number: 5,515,716
[45] Date of Patent: May 14, 1996

[54] METHOD OF DETECTING POLLUTION IN WATER USING SONICATION

[75] Inventors: Edward J. Poziomek, Chesapeake, Va.; Grazyna E. Orzechowska, Las Vegas, Nev.

[73] Assignee: University of Nevada-Las Vegas, Las Vegas, Nev.

[21] Appl. No.: 293,289

[22] Filed: Aug. 22, 1994

[51] Int. Cl.$^6$ ............................. A62D 3/00; C22B 05/00; C02F 01/461

[52] U.S. Cl. ................... 73/61.410; 204/157.15; 204/158.2; 588/227; 588/243

[58] Field of Search ................ 73/61.41; 204/158.2, 204/157.15, 157.42, 130; 588/227, 237, 243, 247

[56]  References Cited

U.S. PATENT DOCUMENTS

| | | | |
|---|---|---|---|
| 3,977,452 | 8/1976 | Knoevenagel et al. | 204/157.1 R |
| 4,755,270 | 7/1988 | Aliotta | 204/157.42 |
| 5,126,020 | 6/1992 | Dames | 204/130 |
| 5,417,825 | 5/1995 | Graham et al. | 204/158.2 |

FOREIGN PATENT DOCUMENTS

| | | | |
|---|---|---|---|
| 2693118 | 1/1994 | France | 588/227 |
| 4210949 | 10/1993 | Germany | 588/227 |
| 5253318 | 10/1993 | Japan | 588/227 |

Primary Examiner—Hezron E. Williams
Assistant Examiner—J. David Wiggins
Attorney, Agent, or Firm—Quirk & Tratos

[57] ABSTRACT

A method for monitoring detecting the presence of pollutants such as chlorinated hydrocarbons in water is provided. In the preferred method, a sample of water is obtained and enclosing or isolating and tested with one or more pollutant sensitive tests. In the preferred method, pH, electrical conductivity and specific ion species sensitive electrode tests are conducted on the sample when testing for the presence of organochlorine compounds. The sample is then sonicated with ultrasound rarefaction and compression waves to cause pollutant decomposition under controlled conditions using a horn probe or cup horn over a length of time at a pulse mode. After sonication, the sample is re-tested, preferably with the same pre-tests of pH, conductivity and electrode measurements. Comparison of the post sonication to pre sonication test results indicates the presence of pollutants, as in the case of the presence of chlorinated hydrocarbons, an increase in the presence of the cl$^-$ ion as indicated by electrode testing, the presence of the pollutant further confirmed by other test results showing a pH decrease and conductivity increase.

13 Claims, 5 Drawing Sheets

FIG. 1A
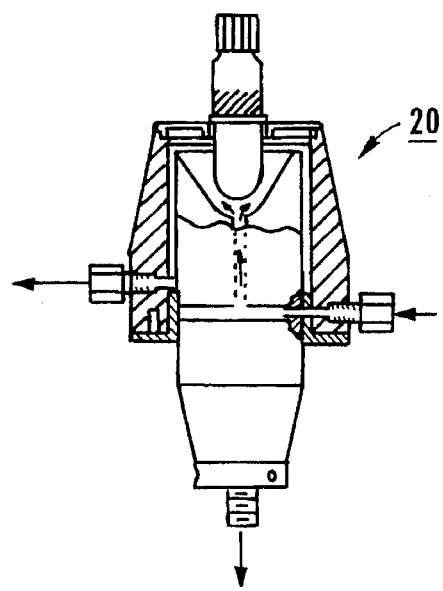
FIG. 1B
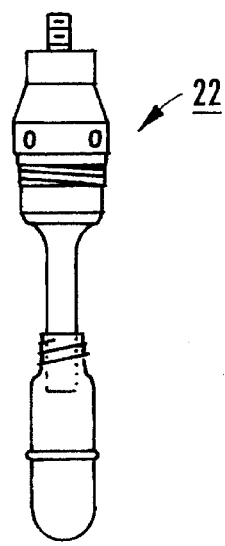
FIG. 2
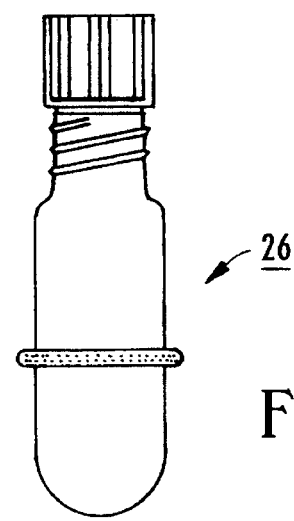
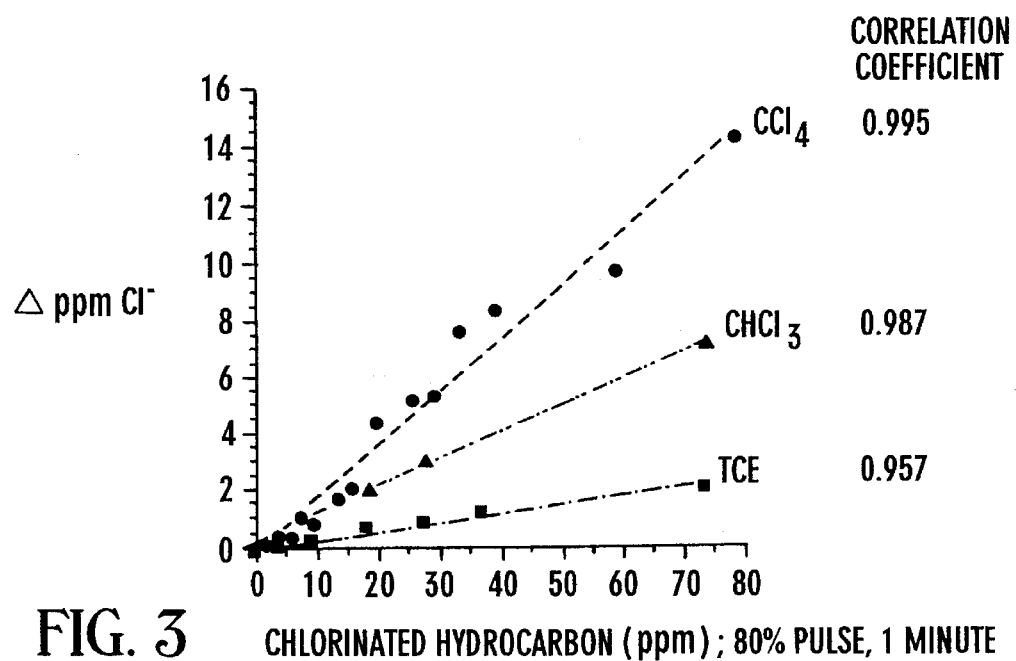
FIG. 3  CHLORINATED HYDROCARBON (ppm); 80% PULSE, 1 MINUTE

METHOD OF DETECTING POLLUTION IN WATER USING SONICATION

FIELD OF THE INVENTION

The present invention relates to field screening methods that focus on detecting the presence of pollutants such as volatile organochlorine pollutants, for example, carbon tetrachloride, chloroform, and trichloroethylene, in water. In particular, the present invention relates to a method in which water is tested, sonicated, and then retested to determine the presence of the above pollutants.

BACKGROUND OF THE INVENTION

Contamination of hazardous waste site ground and surface waters has become a problem demanding great attention. The rapid industrialization of the world has led to the introduction of many pollutants into many of the world's water sources. The contamination of these sources endangers not only humans, but all life relying on these waters.

Typical water tests include those to determine pH, conductivity, temperature, dissolved oxygen, biochemical oxygen demand, chemical oxygen demand, total organic carbon, oxidation-reduction potential, total suspended solids, and turbidity. Further, it is possible to test for the presence of individual pollutants with a variety of analytical methods, including gas and ion chromatography, mass spectrometry, spectroscopy, and fiber optic technology.

These analytical methods are often cumbersome, being both time consuming to set up and run, and often requiring bulky, expensive equipment. These constraints limit the number of tests which may be run, and the locations where the testing may be conducted. Thus, these testing methods also do not normally allow for rapid identification of water pollutants and their concentrations.

No simple testing equipment or methods currently exist for detecting pollutants such as volatile chlorinated hydrocarbons in water quickly and reliably. Further, existing testing equipment and methods do not normally allow for in situ testing of the water, but require that samples be taken from the water source and transported to analytical laboratories sites.

These pollutants are often extremely dangerous humans, and they are commonly found at hazardous waste sites. The detection limits of field methods are not always as low as laboratory methods, but they are useful to screen samples prior to confirmatory laboratory analysis. The advantage is in cost savings by limiting the number of samples sent for laboratory analysis.

SUMMARY OF THE INVENTION

In order to overcome the above stated problems and limitations, there is provided a method for monitoring the presence of pollutants such as volatile chlorinated hydrocarbons in water using ultrasound techniques and commercially available measurement technologies involving the use, for example, of ion specific electrodes, pH electrodes and conductivity.

In the preferred method of the present invention, water sample monitoring is accomplished by comparison of pre and post sonication analysis of the sample. Comparison of the pre and post sonication test results reveals the presence, if any, of pollutants of interest in the sample.

In particular, sonication leads to bond cleavages between atoms in compounds. Thus, while the pollutant itself is often not readily detectable, ions resulting from sonication of the sample containing the pollutant are. In particular, the result of sonication of an organic compound containing chlorine (hereinafter "Cl") normally results in production of the chloride ion (hereinafter "$Cl^-$"). Thus, for example, it is possible to determine the presence of the organochlorine compound carbon tetrachloride ($CCl_4$) in a water sample without directly testing for $CCl_4$. Sonication of the sample containing $CCl_4$ creates $Cl^-$ ions which are readily detectable. For instance, comparison of the levels of $Cl^-$ pre and post sonication may indicate the presence of the pollutant.

In the preferred method of the present invention, the preferred tests conducted on the water sample are pH, conductivity, and $Cl^-$ concentration. Such tests are preferred when monitoring the presence of Cl containing pollutants, i.e. chlorinated hydrocarbons. In the preferred embodiment, these tests are run on the sample both before and after sonication. Increased presence of $Cl^-$ as detected by the electrode, decrease in pH, and increased conductivity all occur as a result of sonication of a water sample containing an organochlorine pollutant. Further, the value increases/decreases in these readings occur in relation to the concentration of the pollutant in the water.

In the present method, sonication is preferably accomplished using a cup horn or horn probe coupled to an ultrasonic power source. Preferably, the sample is cooled via an external device during sonication to reduce heat build-up in the sample. While the frequency of energy during sonication is preferably not varied, pulse and duration of sonication preferably is varied depending on the sample being tested. Variation of sonication parameters is used to optimize the production of identifiable ions, thus increasing the rate of pollutant detection.

The method of the present invention eliminates the need for costly and complex equipment. To the contrary, only simple technology is required to accomplish the monitoring. Further, the simplicity of the detection method of the present invention introduces the possibility of in situ monitoring of water sources, e.g., wells.

Further objects, features, and advantages of the present invention will become apparent from the detailed description of the drawings which follows, when considered with the attached figures.

DESCRIPTION OF DRAWINGS

FIG. 1a illustrates a commercially available cup horn used for sonication;

FIG. 1b illustrates a commercially available horn probe used for sonication;

FIG. 2 illustrates a sonication reaction tube;

FIG. 3 illustrates the changes in $Cl^-$ versus the concentration of TCE, $CHCl_3$, and $CCl_4$ in the range of 3 to 80 ppm;

DETAILED DESCRIPTION OF THE PREFERRED EMBODIMENT

Figure 4:
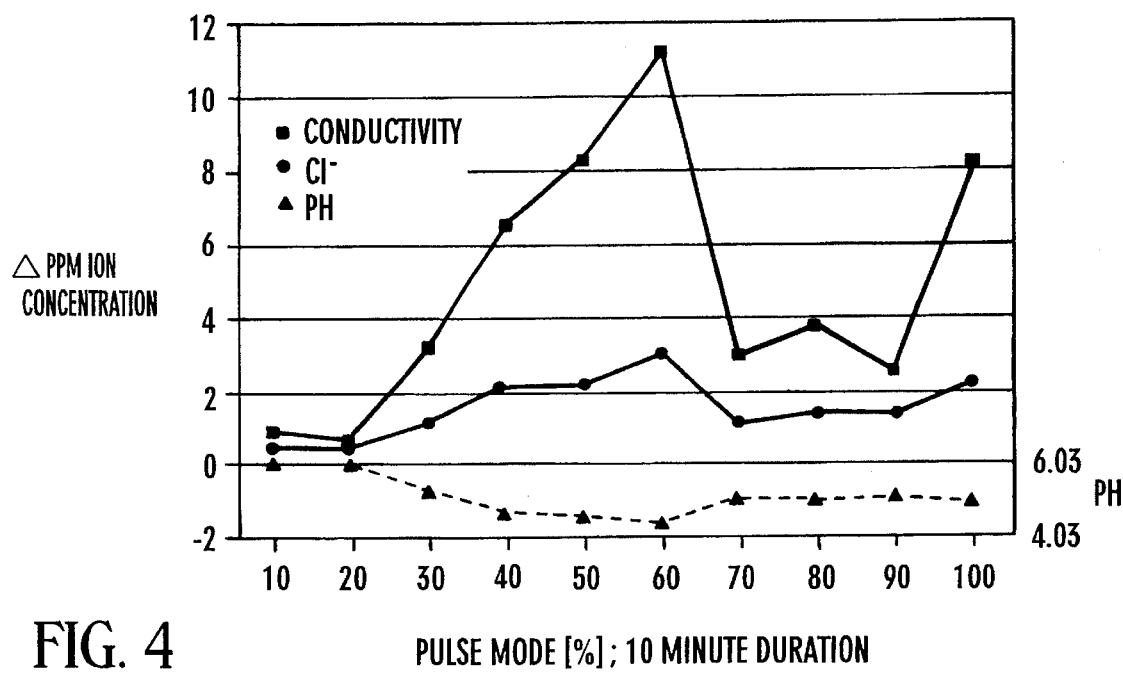
FIG. 4 illustrates the changes in conductivity, ppm $Cl^-$, and pH upon sonication of a water sample containing 37 ppm TCE at various pulse mode percentages using a cup horn.

The present invention comprises a method of detecting the presence of pollutants in water through sonication. Sonication is the process of applying ultrasonic energy to a substance.

The creation and use of ultrasonic energy is well known. Ultrasound is defined as any sound having a frequency beyond which the human ear will not respond. Generally, this frequency is said to be above about 16 kHz. When ultrasonic energy is applied to a fluid, such as water, the alternating waves of energy, called compression and rarefaction cycles, act upon the fluid. If the rarefaction wave is powerful enough, pressures great enough to overcome the molecular forces of bonds in the molecules comprising the fluid may develop. This results in the formation of microbubbles. Then, when the microbubbles encounter the compression cycle of the ultrasonic wave, the bubbles collapse and release large amounts of energy, resulting in the destruction of the molecules.

It has been known for some time that the energy released upon collapse of these microbubbles, which can result in localized temperatures of 5,000 degrees Kelvin and pressures of 1,000 atmospheres, results in the decomposition of certain compounds. Further, the initial decomposition, which creates radicals, often leads to secondary reactions involving the radicals and other species in the fluid. In any instance, ionic products are normally created by the decomposition or bond cleavages.

In the present invention, sonication is used to decompose compounds existing in a water sample. Comparison of pre and post tests upon the sample reveals the presence of pollutants in the sample. As stated above, currently no inexpensive, rapid, and simple method exists for determining the presence of many pollutants in water. In the present method, the presence of a pollutant is not detected directly, but is detected by observing the presence of byproducts resulting from sonication of the sample containing pollutants.

In the preferred method, a cup horn 20 or a ½" horn probe 22, such as those illustrated in FIGS. 1a and 1b, is connected to an ultrasonic power source (not shown). One such power source is the Branson Ultrasonic Corporation Sonifer Model 450. The horns 20, 22 are readily available from Branson Ultrasonic Corporation as part of a package containing the Model 450 Sonifer.

The water sample to be tested is preferably located in a screw-cap vial 26 such as that illustrated in FIG. 2. The exact size and shape of the vial may vary, as may the volume of the sample. In fact, it is contemplated that the sample not even be located in a vial during testing, as described in more detail below.

In order to prevent overheating of the Sample during sonication, the sample may be externally cooled during sonication, and/or a pulse mode may be used. The preferred method of cooling the sample during sonication is to provide a cooling liquid to the cup horn 20. The coolant, such as polyethylene glycol is preferably pumped through a constant temperature circulator such as that identified as Model 1160 manufactured by VWR Scientific Company by a peristaltic pump such as the Cole Parmer Instrument Model No. 7520-25 (as equipped with easy-load pump head Cole Parmer Instrument Model 7518).

When this method of cooling is employed, sonication is accomplished in the cup, whether the horn probe 22 or cup horn 20 is used to sonicate the sample. In the case of the cup horn 20, the sample is simply located in it as illustrated in FIG. 1a. In the case of use of the horn probe 22, the sample is located in a reaction vessel such as the cup horn 20 as shown in FIG. 1a, but sonication occurs by lowering the horn probe 22 into the sample as illustrated in FIG. 1b.

The preferred tests for determining the presence of a pollutant in the present case are conductivity, pH, and $Cl^-$ electrode measurements. These tests are employed because they allow detection of the byproducts of sonication of samples containing organochlorine compounds. It is understood that the exact types of tests employed may vary depending upon the pollutant which is monitored. In the preferred embodiment described herein, test methods for organochlorine compounds are set forth because of their special importance. As stated above, such pollutants are the most commonly found pollutants at hazardous waste sites, and are pollutants which are neutral. Because of this fact, and the fact that current field testing methods for such pollutants are time consuming, the method of the present invention is especially useful in monitoring these pollutants.

when the above-referenced tests are conducted, the following equipment is used. An Orion pH/ISE meter, Model EA 940 (with Orion temperature compensator No. 91700) is preferred. An electrode which is useful in testing for $Cl^-$ is the Orion Solid State Combination ($Cl^-$ ISE), No. 9617, and for testing pH, Orion Ross Combination, No. 8103. An acceptable conductivity meter is an Orion Model 180 (Orion Cell No. 018010, with Orion temperature compensator No. 018870).

In the preferred method of the present invention, a sample of water is obtained. This sample may be taken from ground or surface water, from water in city water systems or the like. The sample is preferably placed in the vial 26 described above for sonication, although it is contemplated that the sample may be temporarily contained in any of a number of manners, especially if the sample is tested in situ in a well, waterline or the like.

Once the water sample is obtained, tests are conducted on the sample in order to determine the initial conditions of the sample. In the preferred method, pH, conductivity, and $Cl^-$ concentration measured via electrode are determined. These baseline levels are recorded for comparison against post-sonication levels.

Sonication of the sample is then performed. Sonication is performed on the sample using the equipment described above, using various sonication times and parameters such as percentage pulse modes. The apparatus described above allows for continuous sonication, or pulse mode sonication. As illustrated by some of the actual experiment data set forth below, the sonication efficiency in bond cleavage, and thus ion formation, varies based on sonication time and percentage pulse, and the compound to be sonicated. Use of pulse mode allows sonication to occur at full/intensity, while limiting temperature build-up in a sample. A sample may need to be subjected to a variety of sonication parameters to achieve the best results. As used herein, best results means the greatest level of change in tested for parameters, and thus detecting of pollutants at lower concentrations, and with greater accuracy.

After sonication, the sample is again tested. In the preferred method, the same pH, conductivity and $Cl^-$ electrode tests are conducted.

Comparison of the pre and post sonication test results indicates the presence, if any, of contaminates in the water sample. For example, if one is monitoring the presence of organochlorine compounds in the sample, the above tests are preferably performed. As sonication of such compounds liberates $Cl^-$ ions, changes in test parameters relating to the increased presence of $Cl^-$ should be observed. In particular, it is known that pH drops, conductivity increases, and ppm $Cl^-$ increases. If comparison of the post to pretest levels of these readings indicates these trends, it is known that a $Cl^-$ containing pollutant was present in the sample originally. The $Cl^-$ electrode test alone is good evidence that a Cl containing pollutant was present. Adding results from the pH and conductivity tests helps to confirm it. Again, such a determination is made without directly testing the substance for particular organochlorine compounds.

Further, by observing the amount or percentage change in these readings, and knowing the expected liberation rate of $Cl^-$ ions from certain compounds under different sonication conditions, one can determine the concentration of the contamination in the sample. FIG. 3 illustrates the changes in $Cl^-$ versus the concentration of TCE, $ChCl_3$, and $CCl_4$ in the range of 3 to 80 ppm. As illustrated, a linear relationship results.

Figure 5:
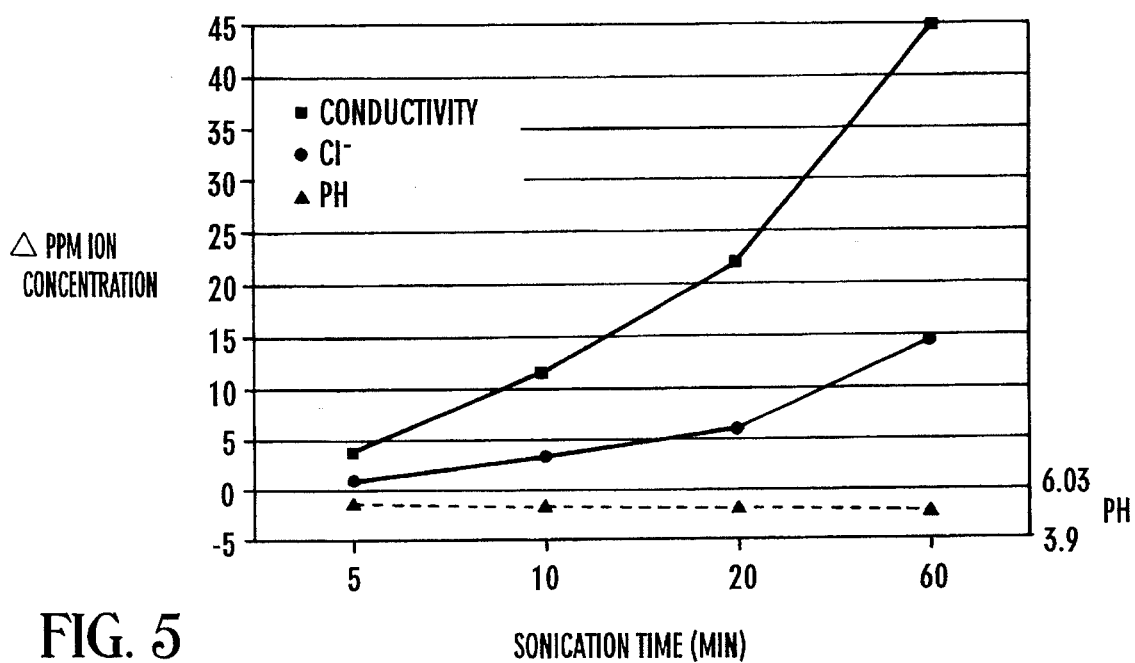
FIG. 5 illustrates the changes in conductivity, ppm $Cl^-$, and pH upon sonication of a water sample containing 37 ppm TCE at 60% pulse mode.

The following examples illustrate the preferred method of the present invention and its results. First, a sample of trichloroethylene (TCE) was prepared in deionized water with a concentration of 37 ppm in the method described below. Sonication of samples at various percentage pulse modes, and for various time periods resulted in various changes in pH, conductivity and $Cl^-$ concentration in the sample as compared to the pre-sonication analysis. The results of these tests are illustrated in FIGS. 4 and 5.

Samples of $CCl_4$ at 40 ppm, chloroform ($CHCl_3$) at 37 ppm, chlorobenzene (Ph-Cl) at 94 ppm, and PCB (3-3'-dichlorobiphenyl and 4-4'-dichlorobiphenyl) at 55 ppm, in addition to the TCE sample, all prepared in deionized water, were also tested. In accordance with the preferred method, pH, conductivity and electrode analysis were conducted, the sample sonicated, and then the sample retested. In each case, stock solutions were prepared in MeOH (methanol), with aliquots of the stock solutions taken for preparation of aqueous solutions at 1:100 dilution. In the case of the PCB samples, a 1:1 combination of the 3,3' and 4,4' isomer PCB's were diluted in 1% aqueous solution of Triton X-100 (trademark, from Aldrich Chemical Company). In each case (except the PCB samples) dilution of the analyte solutions was made to obtain roughly the same concentration (in ppm) of organic chlorine in the samples).

Figure 6:
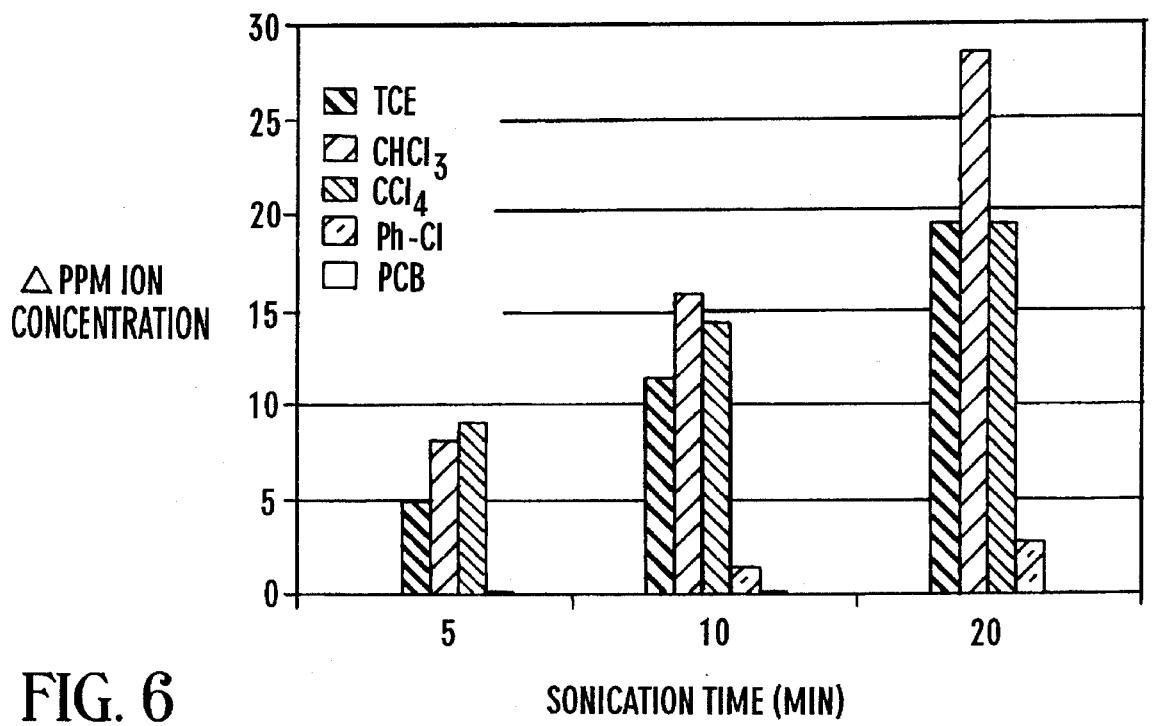
FIG. 6 illustrates the changes in conductivity of individual water samples containing either TCE, $CHCl_3$, $CCl_4$, or Ph-Cl after sonication with a cup horn at 60% pulse mode over 5, 10 and 20 minutes.
Figure 7:
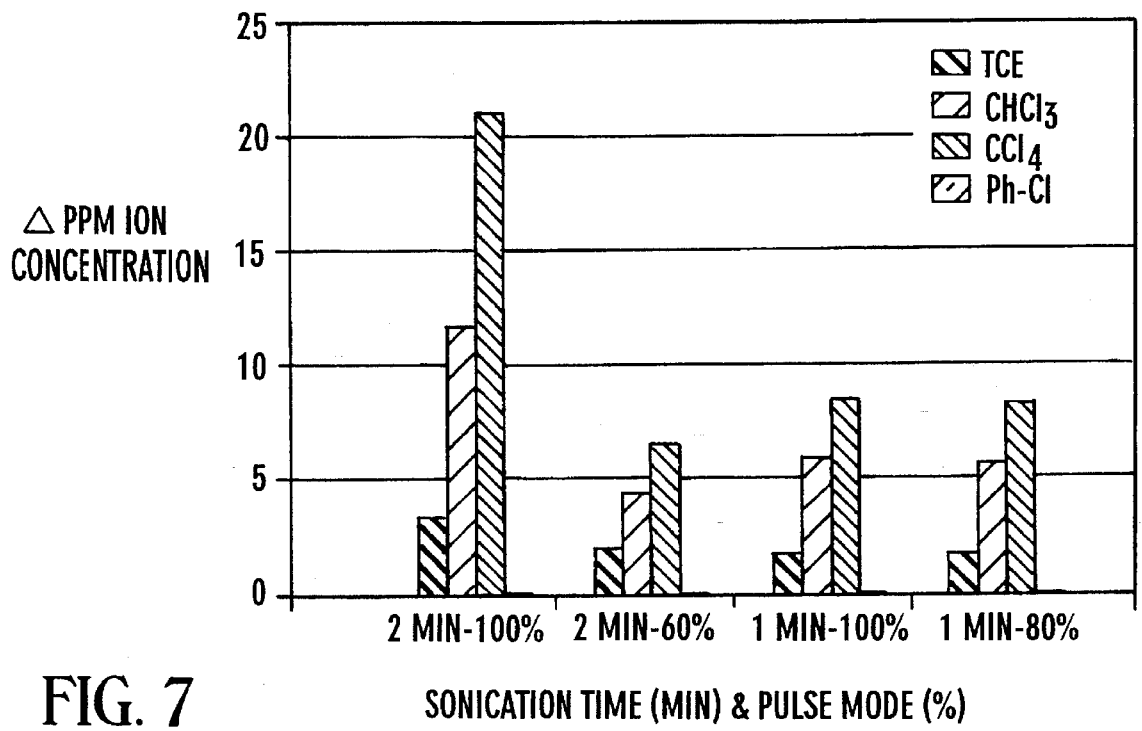
FIG. 7 illustrates the changes in conductivity of individual water samples containing either TCE, $CHCl_3$, $CCl_4$, or Ph-Cl after sonication with a horn probe at various pulse mode percentages and different sonication times.

The conductivity of the samples was tested before and after sonication in the cup horn 20 with a pulse mode of 60%. With the exception of the PCB samples, which after 10 minutes of sonication did not result in higher levels of conductivity, sonication of the samples generally caused higher levels of conductivity. FIG. 6 illustrates the change in conductivity upon sonication of the four samples after various lengths of sonication. With the exception of Ph-Cl at 5 minutes, each of the samples exhibited changes in conductivity after sonication. FIG. 7 illustrates the change in conductivity of the samples resulting from sonication with the horn probe 22, at various sonication time and pulse modes. Again, in each case sonication of each sample caused the conductivity of the sample to increase.

Figure 8:
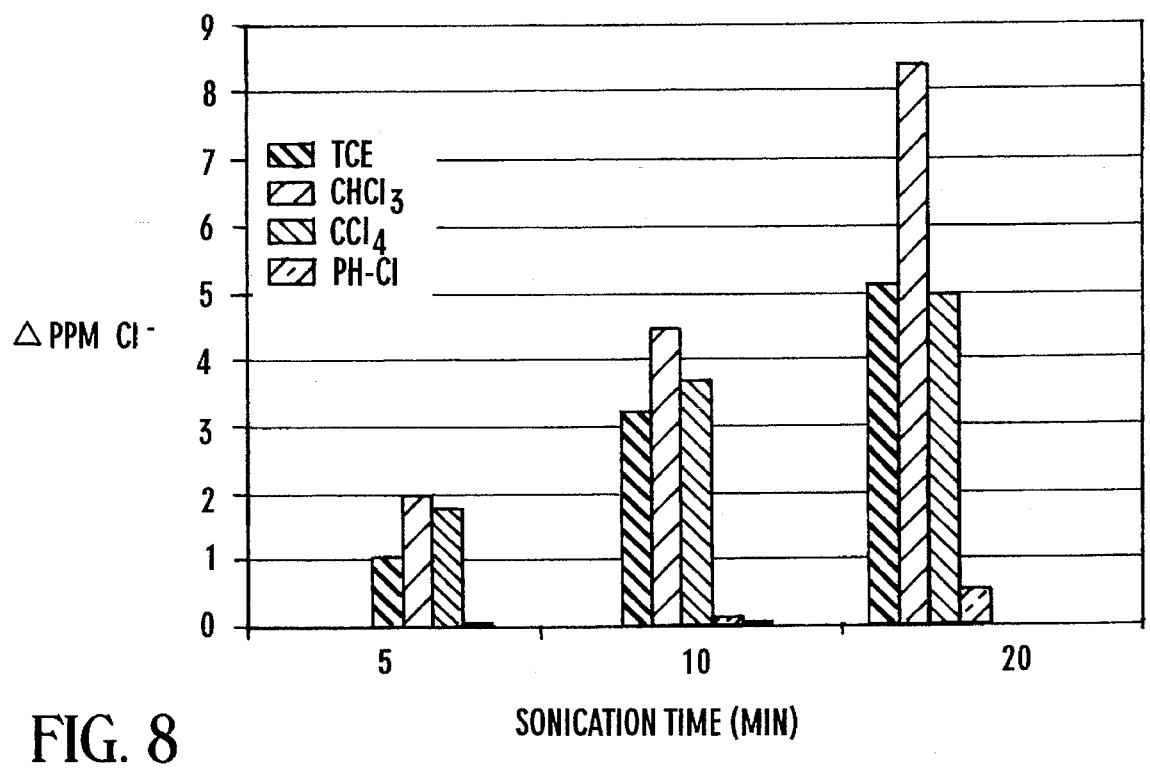
FIG. 8 illustrates the changes in ppm $Cl^-$ of individual water samples containing either TCE, $CHCl_3$, $CCl_4$, or Ph-Cl after sonication with a cup horn at 60% pulse mode over 5, 10 and 20 minutes.
Figure 9:
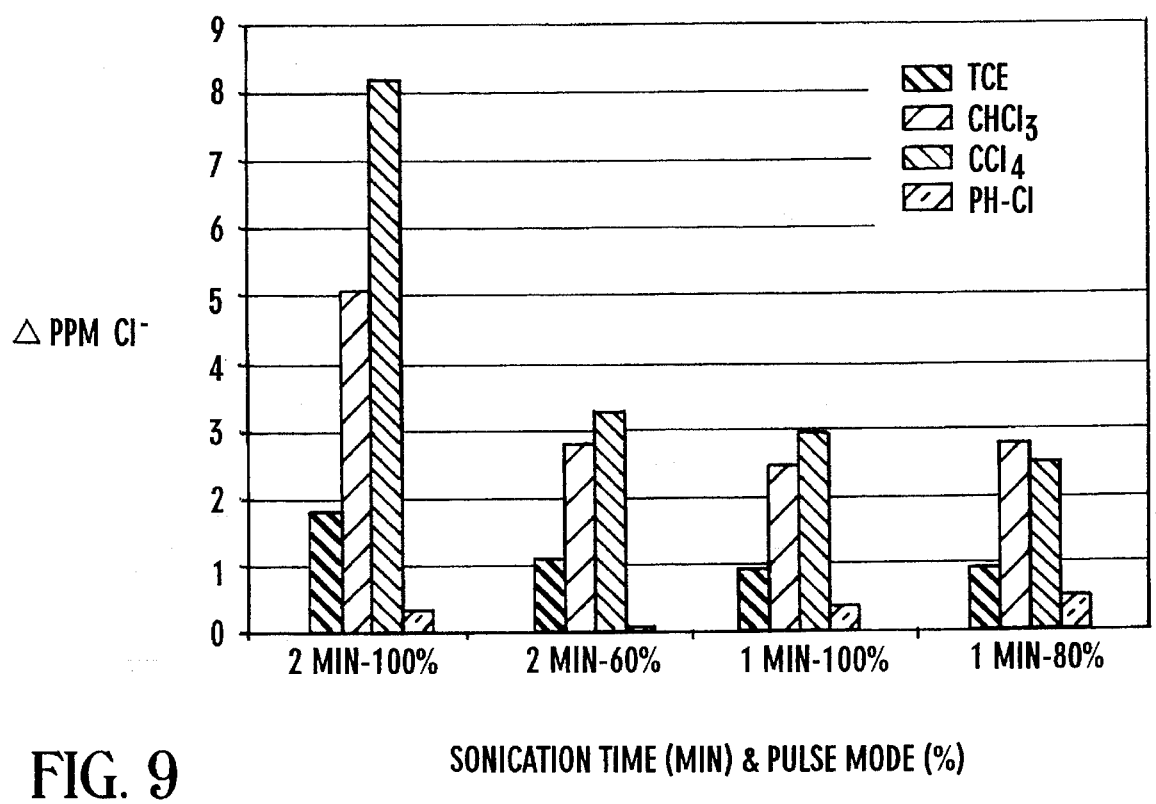
FIG. 9 illustrates the changes in ppm $Cl^-$ of individual water samples containing either TCE, $CHCl_3$, $CCl_4$, or Ph-Cl after sonication with a horn probe at various pulse mode percentages and different sonication times.

The pH and ppm $Cl^-$ of each sample were also tested before and after sonication of the samples as set forth above. FIG. 8 illustrates the change in concentration of $Cl^-$ after sonication of the sample for various lengths of time with the cup horn 20. The ppm of $Cl^-$ in each sample rose after sonication, with the greatest change occurring after 20 minutes sonication. FIG. 9 illustrates the change in ppm $Cl^-$ after sonication with the horn probe 22 at various times and pulse modes. In one instance, samples of each solution were tested via ion chromatography after sonication, with results compared against the electrode test results. The ion chromatography results confirmed the accuracy of the $Cl^-$ electrode testing.

Figure 10:
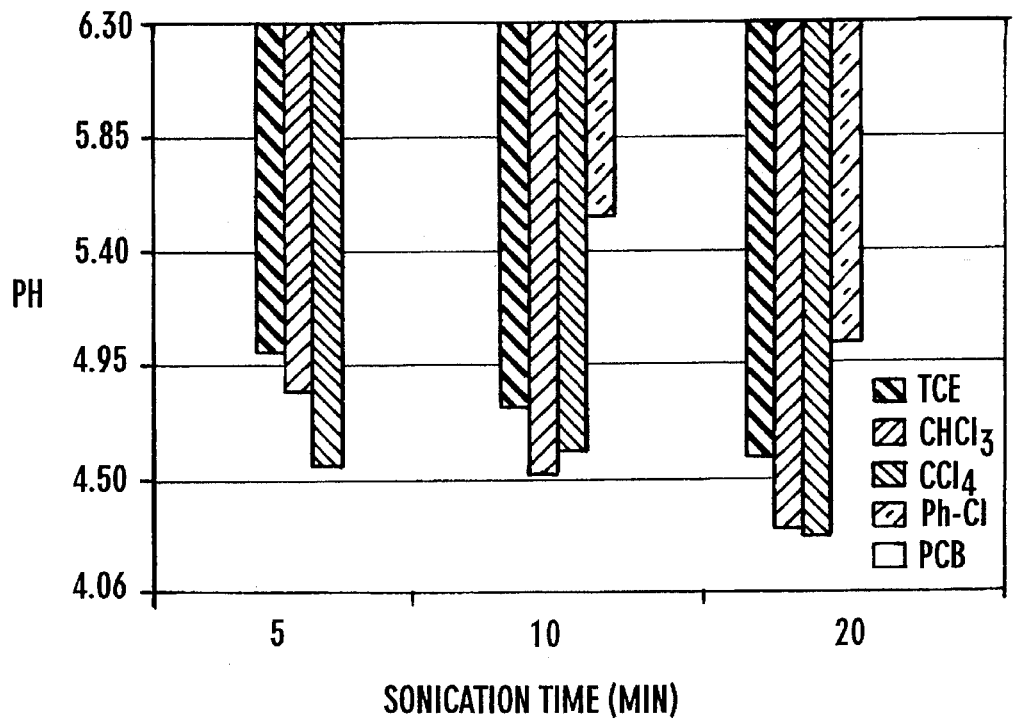
FIG. 10 illustrates the changes in pH of individual water samples containing either TCE, $CHCl_3$, $CCl_4$, or Ph-Cl after sonication with a cup horn at 60% pulse mode over 5, 10 and 20 minutes.
Figure 11:
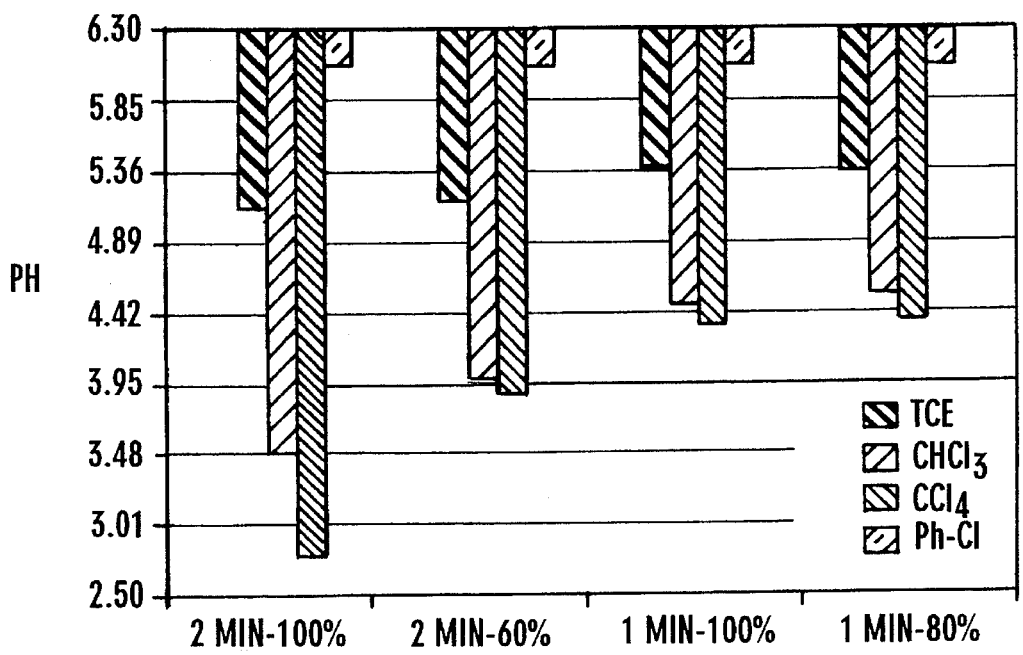
FIG. 11 illustrates the changes in pH of individual water samples containing either TCE, $CHCl_3$, $CCl_4$, or Ph-Cl after sonication with a horn probe at various pulse mode percentages and different sonication times.

FIG. 10 illustrates the change in pH in each sample after sonication in the cup horn 20 at various times at 60% pulse mode. As expected from the creation of $Cl^-$ ions during sonication, the pH of the sample decreased in all cases. FIG. 11 illustrates the results of the change in pH of the samples as a result of sonication with the horn probe 22. Sonication with the horn probe also caused a lower pH in the samples.

Similar tests and results were performed on sonication of samples of TCE (37 ppm), $CCl_4$ (40 ppm), $CHCl_3$ (37 ppm) and Ph-Cl (94 ppm) prepared in tap water. The changes in conductivity and pH were much lower after sonication of these samples than those prepared in deionized water. It is believed that the smaller changes are a result, at least in part, of the initial pH of the water into which the pollutant was placed being 8.4 for the tap water compared to 6.5 for the deionized water. In any case, attention may need to be given to the pH of real world samples in order to obtain proper results using the method of the present invention. This is because of buffering and inhibiting effects of some water components, i.e., carbonates and bicarbonates.

In each of the above examples, the electrode testing conducted was for the $Cl^-$ ion. As stated above, the testing conducted was to determine whether the presence of neutral inorganic pollutants contain Cl. Because the common product of sonication of compounds including Cl is the $Cl^-$ ion, testing was for the $Cl^-$ ion. It should be understood, however, that other electrode testing could be conducted in accordance With the present method. For example, if the particular compound which is being monitored contains another inorganic element, an electrode which is sensitive to the detection of that element can be used. Any number of such electrode tests can be conducted, and in fact, numerous different electrode tests can be conducted on a single sample in order to detect the presence of a wide variety of compounds.

It is also contemplated that the method of the present invention be accomplished with apparatus other than that described above. In particular, it is desirable for the apparatus to be small enough to allow in situ monitoring in small wells and the like. In such instances, the sample need not necessarily be located in a vial but may simply be isolated in a manner to allow sonication and testing without dilution or contamination via surrounding substances. Apparatus including the testing probes and sonication horns in such an instance would preferably be located in situ, with remote data receiving and processing equipment located in a convenient location.

It will be understood that the above described arrangements of apparatus and the method therefrom are merely illustrative of applications of the principles of this invention and many other embodiments and modifications may be made without departing from the spirit and scope of the invention as defined in the claims.

We claim:

1. A method for monitoring pollutants in water, comprising the steps of:
   a) obtaining and enclosing or isolating a sample of water to be tested;
   b) conducting a pollutant sensitive test on the sample to obtain pre-sonication test results, the test selected from the group consisting of pH, electrical conductivity, and specific ion species sensitive electrode testing;
   c) sonicating the sample with ultrasound rarefaction and compression waves to cause pollutant decomposition under controlled conditions; and
   d) retesting the sample with each pollutant sensitive test that was conducted on the sample before the sonicating step to obtain post-sonication test results.

2. The method of claim 1, wherein a horn probe is used in said sonicating step.

3. The method of claim 1, wherein a cup horn is used to in said sonicating step.

4. The method of claim 1, wherein the pulse percentage and time of sonication are varied to achieve maximum difference in the test results between the pre- and post-sonication tests.

5. The method of claim 1, wherein said sample is located in a container.

6. The method of claim 1, wherein the pollutants to be tested for are organochlorine compounds.

7. A method of detecting organochlorine pollutants in water comprising the steps of:
   a) obtaining and enclosing or isolating a water sample;
   b) conducting a pollutant sensitive, ion-specific $Cl^-$ electrode test to obtain pre-sonication test results;
   c) sonicating the sample;
   d) conducting a pollutant sensitive, ion specific $Cl^-$ electrode test after sonication of the sample to obtain post sonication test results; and
   e) identifying the presence of organochlorine pollutants in the water, wherein if said sample contains said pollutants, comparison of the pre- and post-sonication test results indicates an increase in $Cl^-$ concentration.

8. The method of claim 7, wherein a pH test is conducted both before the sonication step and after the sonication step in addition to the electrode test.

9. The method of claim 7, wherein an electrical conductivity test is conducted both before the sonication step and after the sonication step in addition to the electrode test.

10. The method of claim 7, wherein a pH and an electrical conductivity test are each conducted before the sonication step and after the sonication step in addition to the electrode test.

11. The method of claim 7, wherein parameters of sonication selected from the group consisting of time, intensity, and pulse mode are varied to achieve maximum differences in the pre- and post-sonication test results.

12. A method for detecting pollutants in water, comprising the steps of:
   a) obtaining and enclosing or isolating a sample of water to be tested;
   b) conducting a pollutant sensitive test on the sample to obtain pre-sonication test results;
   c) sonicating the sample with ultrasound rarefaction and compression waves to cause pollutant decomposition under controlled conditions;
   d) retesting the sample with each pollutant sensitive test that was conducted on the sample before the sonicating step to obtain post-sonication test results; and
   e) comparing the results of the pre-sonication test results to the post-sonication test results to determine the presence of pollutants.

13. The method of claim 12, wherein the test is selected from the group consisting of pH, specific in species sensitive electrode testing, and electrical conductivity.

* * * * *